(12) United States Patent
Flytzani-Stephanopoulos et al.

(10) Patent No.: US 9,090,833 B2
(45) Date of Patent: Jul. 28, 2015

(54) CONVERTING BIOMASS TO GASEOUS FUEL HYDROCARBONS

(75) Inventors: Maria Flytzani-Stephanopoulos, Winchester, MA (US); Branko Zugic, Somerville, MA (US); Brian Ricks, Cambridge, MA (US); Gregory Stephanopoulos, Winchester, MA (US)

(73) Assignee: Tufts University, Medford, MA (US)

( * ) Notice: Subject to any disclaimer, the term of this patent is extended or adjusted under 35 U.S.C. 154(b) by 919 days.

(21) Appl. No.: 13/202,239

(22) PCT Filed: Feb. 23, 2010

(86) PCT No.: PCT/US2010/025061
§ 371 (c)(1),
(2), (4) Date: Oct. 31, 2011

(87) PCT Pub. No.: WO2010/096812
PCT Pub. Date: Aug. 26, 2010

(65) Prior Publication Data
US 2012/0035403 A1      Feb. 9, 2012

Related U.S. Application Data

(60) Provisional application No. 61/154,598, filed on Feb. 23, 2009, provisional application No. 61/176,605, filed on May 8, 2009.

(51) Int. Cl.
*C07C 1/00* (2006.01)
*C10G 3/00* (2006.01)
*C07C 1/207* (2006.01)

(52) U.S. Cl.
CPC ............... *C10G 3/45* (2013.01); *C07C 1/2078* (2013.01); *C10G 3/47* (2013.01); *C10G 3/49* (2013.01); *C10G 3/50* (2013.01); *C07C 2521/00* (2013.01); *C07C 2521/16* (2013.01); *C07C 2521/18* (2013.01); *C07C 2523/02* (2013.01); *C07C 2523/14* (2013.01); *C07C 2523/36* (2013.01); *C07C 2523/42* (2013.01); *C07C 2523/44* (2013.01); *C07C 2523/46* (2013.01); *C07C 2523/50* (2013.01); *C07C 2523/52* (2013.01); *C07C 2523/70* (2013.01); *C07C 2523/72* (2013.01); *C07C 2527/04* (2013.01); *C07C2529/00* (2013.01); *C07C 2529/04* (2013.01); *C10G 3/42* (2013.01); *C10G 2300/1014* (2013.01)

(58) Field of Classification Search
CPC .............. C10G 3/42; C10G 3/46; C10G 3/47; C10G 3/50; C10G 45/62; C10G 2300/108; C10G 2400/20; Y02E 50/10
USPC ............. 585/240, 242, 638, 700; 44/605, 606
See application file for complete search history.

(56) References Cited

U.S. PATENT DOCUMENTS 4,443,639 A      4/1984  Pesa et al.
4,992,605 A  *  2/1991  Craig et al. ................ 585/240
(Continued)

FOREIGN PATENT DOCUMENTS

WO    2007/068798    6/2007
WO    2008/103204    8/2008

*Primary Examiner* — Nina Bhat
(74) *Attorney, Agent, or Firm* — Cesari and McKenna, LLP

(57) ABSTRACT

A method for producing a $C_{1-5}$ hydrocarbon from a solution containing a $C_{2-6}$ carboxylic acid or a $C_{2-6}$ carboxylate which is derived from biomass by contacting the solution with a solid catalyst to decarboxylate the $C_{2-6}$ carboxylic acid or the $C_{2-6}$ carboxylate, thereby forming a $C_{1-5}$ hydrocarbon.

25 Claims, 3 Drawing Sheets

(56) References Cited

U.S. PATENT DOCUMENTS

| | | | |
|---|---|---|---|
| 5,705,722 A * | 1/1998 | Monnier et al. | 585/240 |
| 7,459,597 B2 * | 12/2008 | Koivusalmi et al. | 585/733 |
| 7,491,858 B2 * | 2/2009 | Murzin et al. | 585/240 |
| 7,691,159 B2 * | 4/2010 | Li | 44/605 |
| 2007/0010682 A1 * | 1/2007 | Myllyoja et al. | 554/174 |
| 2007/0135669 A1 * | 6/2007 | Koivusalmi et al. | 585/331 |

* cited by examiner

CONVERTING BIOMASS TO GASEOUS FUEL HYDROCARBONS

STATEMENT AS TO FEDERALLY-SPONSORED RESEARCH

This invention was supported by 0304515 awarded by the National Science Foundation. The government has certain rights in the invention.

CROSS-REFERENCE TO RELATED APPLICATIONS

This application claims the benefit of International Application No. PCT/US2010/025061, filed Feb. 23, 2010, which claims the priority of U.S. Provisional Application Ser. Nos. 61/154,598 and 61/176,605, filed Feb. 23, 2009 and May 8, 2009, respectively. The contents of all three prior applications are incorporated herein by reference.

FIELD OF THE INVENTION

The invention relates to methods of converting biomass to gaseous fuel hydrocarbons.

BACKGROUND

Declining petroleum resources have heightened the interest in biomass as a renewable energy source. Various processing options for biomass have been explored, including gasification to form synthesis gas, pyrolysis and liquefaction to generate bio-oils, and fermentation of sugars formed through hydrolysis of cellulosic and hemicellulosic biomass. The above processing options are described in detail in Huber, G. W. et al., *Chem. Rev.* 106 (2006) 4044-4098. There is a need in seeking other potentially inexpensive and efficient methods of converting biomass to fuels.

SUMMARY

In one aspect, the invention relates to a method of converting biomass to fuels (e.g., short-chain hydrocarbon fuels, in particular, a method of decarboxylating a $C_{2-6}$ carboxylic acid or a $C_{2-6}$ carboxylate. More specifically, the method includes providing a solution containing a $C_{2-6}$ carboxylic acid or a $C_{2-6}$ carboxylate that is derived from biomass and contacting the solution with a solid catalyst to form a $C_{1-5}$ hydrocarbon.

The term "biomass" includes but is not limited to whole plants or parts thereof, organic matter in municipal solid wastes, photosynthetic organisms (e.g. cyanobacteria, macro-algae, and micro-algae) or parts thereof, carbohydrate compounds such as simple sugars (e.g., glucose, xylose, mannose, and arabinose) and their polymers, such as starch, cellulose, hemicellulose, and lignin. The term "solid catalyst" refers to a catalyst in the form of a solid at room temperature and 1 atm. The term "carboxylate" refers to a conjugate base or a salt of the corresponding carboxylic acid (e.g. hydroxybutyrate, sodium acetate, potassium butyrate, or ethyl propionate).

The carboxylic acids can be obtained from biomass by a variety of approaches such as thermochemical, catalytic, and biochemical. See, e.g., Corma, A. et al., *J. Catal.* 257 (2008): 163-171. For instance, short-chain aliphatic carboxylic acids (e.g., butyric acid) or their salts (e.g., butyrate) can be obtained from sugars by hydrolysis followed by fermentation. In another example, municipal waste is first converted to synthesis gas, and the synthesis gas is then converted to a carboxylic acid mixture.

The method of this invention can be performed under different conditions. The solution containing the carboxylic acid or the carboxylate can be carried by a gas to effect contact with the solid catalyst. The gas can be hydrogen, an inert gas or a mixture of an inert gas and hydrogen. The solution (e.g., an aqueous solution) can be brought into contact with the solid catalyst at 25-500° C. (e.g., 200-350° C. or 250-400° C.) and at 1-30 atm (e.g., 1-10 atm or 5-15 atm). The solid catalyst includes a metal (e.g., Fe, Co, Ni, Mn, Ru, Rh, Pd, Re, Os, Ir, Pt, Sn, Cu, Ag, Au, or a combination thereof) and a substrate (e.g., a metal oxide, metal sulfide, metal nitride, metal carbide, a zeolite, a molecular sieve, a perovskite, a clay, a carbonaceous material, or a combination thereof).

The method can further include purifying thus-obtained $C_{1-5}$ hydrocarbon by removing the other product $CO_2$ via liquefaction, neutralization, or any other suitable techniques. It can also include recycling the gaseous carrier gas back to the reactor; and/or using some part of it with the $CO_2$ produced to make fuels or chemicals. The condensed liquid effluent can be further treated and discharged or returned to the fermentor downstream processing units.

The term "metal" refers to an elemental metal, a metal alloy, and a metal-containing compound (e.g., a metal oxide or an elemental metal coated with its oxide) that is reducible to form an elemental metal under the conditions described herein. The term "carbonaceous material" refers to material that is rich in carbon, e.g., having 70% of elemental carbon or more by weight. Examples of carbonaceous materials include but are not limited to activated carbon, graphite, charcoal, carbon black, carbon nanotubes, carbon fibers, or a combination thereof.

One advantage of the above-described method is that the fuels thus produced are rich in gaseous hydrocarbons such as propane and butane. The gaseous hydrocarbons are particularly desirable since they can easily be integrated into the current pipeline infrastructure. Indeed, propane and butane mixtures comprise the Liquified Petroleum Gas (LPG). Another advantage is that the method, unexpectedly, has a high selectivity for decarboxylation. Namely, other reactions such as decarbonylation are unlikely to take place. A hydrocarbon product rich in alkanes is produced when hydrogen is used as the carrier gas. However, a mixture of alkanes and alkenes, e.g. propane and propylene, is possible, by using an inert carrier gas.

Also within the scope of the invention is a solid catalyst described above.

The details of one or more embodiments are set forth in the accompanying description below. Other aspects, features, and advantages will be apparent from the following drawing, detailed description of embodiments, and also from the appending claims.

DETAILED DESCRIPTION

This invention relates to a method of decarboxylating a carboxylic acid (e.g., butyric acid) or its salt (e.g., butyrate) to form a hydrocarbon fuel, e.g., a propane rich fuel. The method can thus be applied to make liquefied petroleum gas (LPG).

The method includes first providing a solution containing one or more short-chain carboxylic acids (e.g., $C_{2-6}$ carboxylic acids) or their salts (e.g., $C_{2-6}$ carboxylates) that are derived from biomass and then contacting the solution, in vapor or liquid phase, with a solid catalyst to form one or more short-chain hydrocarbons (e.g., methane, ethane, ethylene, propane, propene, butane, butene, etc.). Preferably, the catalyst has a high and stable decarboxylation activity at moderate temperatures (e.g., not higher than 400° C.) and moderate pressures (e.g., not higher than 20 atm). Higher pressures (e.g., ~30 atm) may be used to, e.g., keep the solution in liquid phase during the decarboxylation reaction. The solution can be either aqueous or organic. Before contacting the solution with the catalyst, one can first fully or partially gasify the solution by adjusting the temperature and pressure. Hydrogen gas (99.99%) can be used as a carrier and reactant gas to bring the vapor-phase solution into contact with the catalyst. An inert gas, e.g., nitrogen ($N_2$), helium (He), and argon (Ar), can also be used as a carrier gas and to control the pressure of the decarboxylation process. Hydrogen can also be used to pretreat (e.g. to reduce) the catalyst, to keep the catalyst in its reduced form, or to catalyze the hydrogenation of the carboxylic acids to afford the corresponding alkanes.

Figure 1:
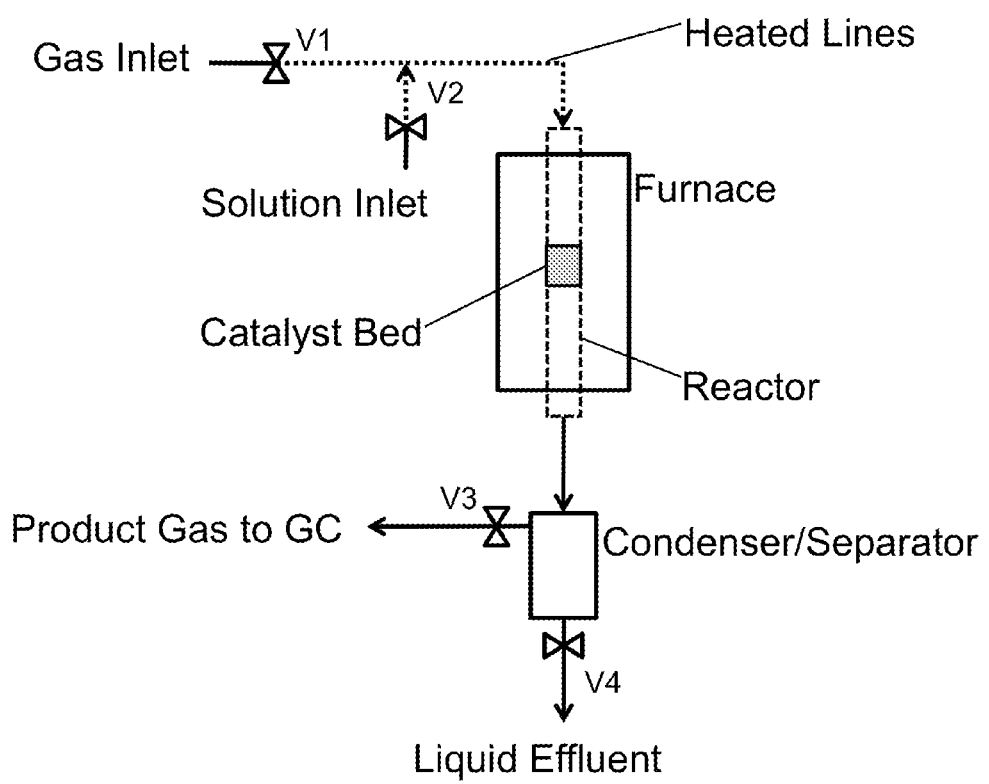
FIG. 1 is a schematic of a continuous flow reactor system used in an embodiment of the invention.

In one embodiment, the method of this invention is carried out in a continuous, tubular reactor system as shown in FIG. 1. This system can also be used for testing the yield and selectivity of decarboxylation reactions under different conditions. Generally, a gas flow (e.g., 99.99% $H_2$ or 5% $H_2$/He) is supplied at a selected pressure (e.g., 1 to 7 atm) and at a predetermined flow rate. The flow rate through the reactor can be adjusted by controlling an upstream mass flow controller at the gas inlet or a downstream double-sided needle valve (see "V3" in FIG. 1) and can be measured at the outlet of the reactor system via a bubble meter. A liquid containing the carboxylic acid or carboxylate (e.g., an aqueous butyric acid solution) can be supplied by a high-performance liquid chromatography pump. Both the gas and liquid feeds lead to a tubular furnace-encased reactor where the liquid is partially or fully vaporized. Also shown in FIG. 1, at the reactor outlet, a gas and liquid mixture flows into a condenser (e.g., a 150 mL stainless steel cylinder at room temperature). The gas exits the system at the top of the condenser and enters a gas chromatograph (GC) while the liquid is collected and may be sampled via a second double-sided needle valve (see "V4" in FIG. 1) at the bottom of the condenser and collected in a glass vial. A needle valve allows a small amount of liquid flow out of the reactor system without a significant loss of the system pressure. The liquid samples in the vial can be analyzed by a GC equipped with a flame ionization detector.

The decarboxylation of carboxylic acid or carboxylate is carried out using various supported metal catalysts. In one embodiment, the reactor described above is first loaded with a metal catalyst and quartz beads, the latter being 1.5 times the weight of the former, for even distribution of the catalyst within the reactor. The furnace surrounding the reactor is then heated at a selected rate (e.g., 2° C. per minute) from room temperature up to the reaction temperature (e.g., 200-400° C.) with a pretreatment gas flowing in at a selected rate (e.g., 30 mL/min) and at a pressure ranging from 1 to 20 atm. To ensure uniform heating and to provide sufficient time for catalyst reduction, once the reactor is heated to the desired reaction temperature, it can be kept at that temperature for a certain period of time (e.g., 30 minutes) prior to introducing the carboxylic acid or carboxylate solution. When the catalyst is to be reduced before the decarboxylation reaction, $H_2$ gas or a $H_2$/He (or $N_2$) mixture can be used as a pretreatment gas. On the other hand, when the catalyst is not to be reduced, pure He or $N_2$ can be used as the pretreatment gas. The pretreatment gas may be the same as or different from the carrier gas described above. For example, a 5% $H_2$/He (or $N_2$) gas stream can be used as both the pretreatment gas and carrier gas of the solution. As another example, $H_2$ is used as the pretreatment gas when the reactor is heated to and kept at a predetermined decarboxylation temperature for 30 min, and then is also used as a carrier/reactant gas for the solution when the decarboxylation reaction takes place.

One can also control the product yield of the decarboxylation reaction by varying the concentration or flow rate of the carboxylic acid/carboxylate solution. In one embodiment, an aqueous solution of butyric acid is prepared with an acid concentration ranging from 4 wt % to 90 wt % and is pumped into a heated reactor at a rate of 0.01 to 0.05 mL/min. The vapor stream coming out of the outlet of the reactor can be cooled in a condenser where the liquid and gas phases of the stream separate. As already described above, the liquid phase can be sampled at regular intervals throughout the decarboxylation process while the gas phase flows from the top of the condenser to be collected or analyzed by an on-line instrument such as a gas chromatograph (GC) equipped with a flame ionization detector (FID). The collected liquid samples can be analyzed with, e.g., a GC with FID.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

A 1 wt % $Pt/Al_2O_3$ catalyst was prepared in house by incipient wetness impregnation. To prepare the catalyst, the substrate $Al_2O_3$ (Puralox®, $S_{BET}$=210 $m^2$/g) was impregnated with an aqueous solution of $Pt(NH_3)_4(NO_3)_2$, the volume of which equaled the total pore volume of $Al_2O_3$ (~0.5 ml/g), at room temperature. After impregnation, the sample was dried in vacuum at 80° C. overnight and calcined in air at 200° C. for 1 h. The resulting material had very highly dispersed Pt on the alumina surface.

The decarboxylation of aqueous solutions of butyric acid was performed over the $Pt/Al_2O_3$ catalyst at atmospheric pressure in the continuous flow reactor described above. The catalyst loading was kept constant at 0.2 g throughout. The weight hourly space velocity (WHSV), defined here as grams of acid per gram catalyst per hour ($g_{acid}/g_{cat}$/hr) or as $h^{-1}$ for brevity, was varied (0.9-2.7 $h^{-1}$) by changing the feed concentration of the reactant butyric acid solution (30-90 wt % butyric acid in water). Prior to reaction the catalyst was reduced with 99.99% $H_2$ gas. In a reduction treatment, the catalyst sample was heated to 300° C. at a rate of 2° C. per minute and held at 300° C. for 30 minutes under a flow of $H_2$ gas flowing at 50 mL/min at atmospheric pressure. The pretreatment gas was also used as a carrier/reactant gas for the decarboxylation reaction. The reaction temperature was varied from 300° C. to 400° C., and cycled back to 350° C. to check for deactivation.

Figure 2:
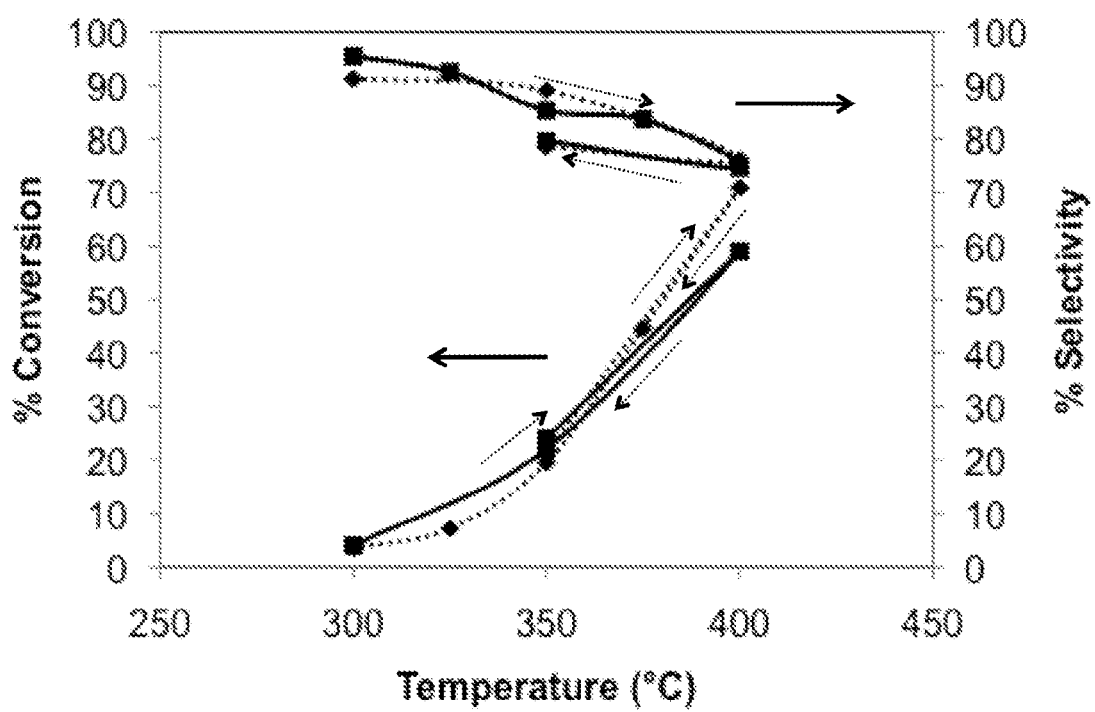
FIG. 2 is a plot of butyric acid conversion/propane selectivity as a function of temperature, demonstrating the performance of 1 wt % $Pt/Al_2O_3$ in catalyzing decarboxylation of butyric acid to form propane. Reaction conditions: 1 atm; 99.99% $H_2$ gas; 300-400° C.; 30 wt % butyric acid (corresponding to WHSV=0.9 $h^{-1}$; diamonds) and 90 wt % butyric acid (corresponding to WHSV=2.7 $h^{-1}$; squares).

The $Pt/Al_2O_3$ catalyst reached a steady state after about 30 minutes of time-on-stream. The major product was found to be propane with the two different space velocities resulting in similar conversions, as indicated in FIG. 2. Unless otherwise specified, the gaseous products described here and below do not include $CO_2$, and thus the volume percentages provided here and below are not calculated to include $CO_2$. Increasing temperature resulted in higher conversions with a slight decrease in propane selectivity. Some permanent loss of selectivity to propane was observed for both space velocities upon reaction at 400° C. Increasing temperature most notably increased the conversion of butyric acid to cracking products (i.e. ethane and methane, up to 6% and 15% conversion, respectively). However, under the higher space velocity conditions, conversion to $C_4$ products was also observed, which did not subside upon cycling the temperature back to 350° C. The catalyst showed strong stability as its activity (60% conversion) did not decrease during 15 hours of time on stream at 400° C. and WHSV=2.7 $h^{-1}$.

Table 1 below shows the selectivity to different gaseous hydrocarbons for each test. As indicated by the results listed in Table 1, the $Pt/Al_2O_3$ catalyst is highly selective for catalyzing decarboxylation of butyric acid to form propane. The small amounts of methane and ethane indicate the presence of carbon cracking side reactions at higher temperatures. A small amount of the butyric acid was also hydrogenated to yield butane.

TABLE 1

Product selectivities using 1 wt % $Pt/Al_2O_3$

| Temp (° C.) | Methane (%) | Ethane (%) | Propylene (%) | Propane (%) | Butane (%) |
|---|---|---|---|---|---|
| WHSV = 0.9 $h^{-1}$ | | | | | |
| 300 | 4 | 0 | 0 | 96 | 0 |
| 325 | 6 | 2 | 0 | 93 | 0 |
| 350 | 5 | 3 | 0 | 85 | 6 |
| 375 | 6 | 5 | 0 | 84 | 6 |
| 400 | 13 | 7 | 0 | 75 | 5 |
| 350 | 5 | 3 | 0 | 80 | 12 |
| WHSV = 2.7 $h^{-1}$ | | | | | |
| 300 | 7 | 2 | 0 | 91 | 0 |
| 350 | 6 | 4 | 1 | 89 | 0 |
| 400 | 15 | 6 | 0 | 76 | 3 |
| 350 | 6 | 3 | 1 | 79 | 11 |

Reaction conditions: 1 atm; 99.99% $H_2$ carrier gas; 300-400° C.; 30 wt % and 90 wt % butyric acid in water (0.01 ml/min.)

The liquid samples collected from the reactor did not show any other products upon analysis by gas chromatography. Only butyric acid was detected, indicating high selectivity towards the hydrocarbon gases.

EXAMPLE 2

Figure 3:
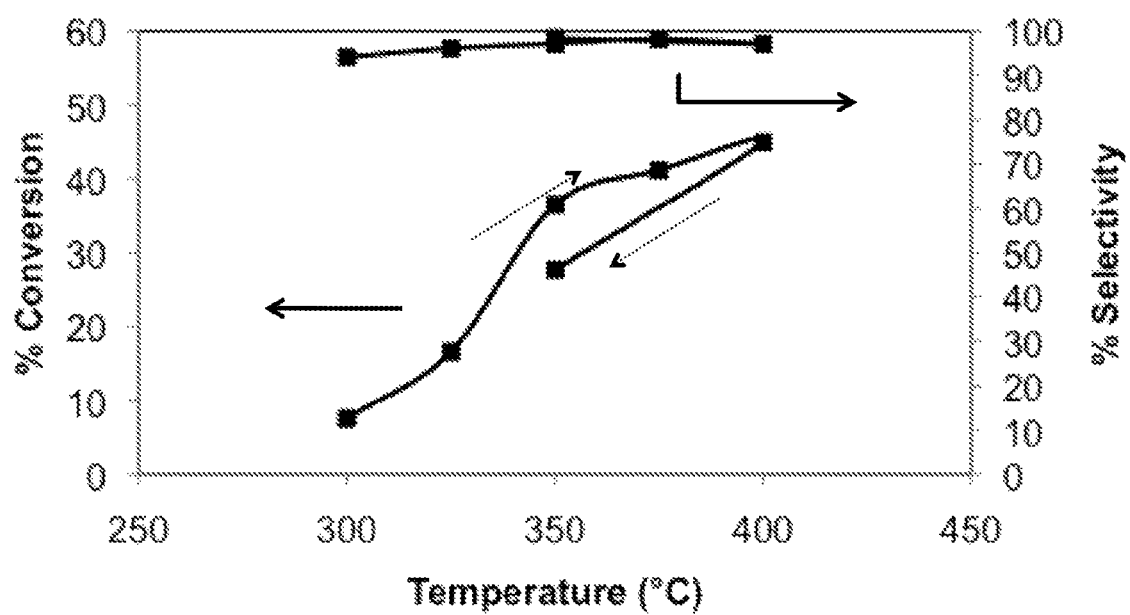
FIG. 3 is a plot of butyric acid conversion/propane selectivity as a function of temperature, demonstrating the performance of 5 wt % Pd/C in catalyzing decarboxylation of butyric acid to form propane. Reaction conditions: 1 atm; 99.99% $H_2$ carrier gas; 30 wt % butyric acid solution; WHSV=0.9 $h^{-1}$.

The decarboxylation of butyric acid was carried out using a 5 wt % Pd/C catalyst obtained from Alfa Aesar. The catalyst was reduced at 300° C. using a ramp of 2° C. per minute under 99.99% hydrogen gas. The catalyst was tested using a feed solution of 30 wt % butyric acid at a temperature of 300-400° C., using hydrogen as a carrier/reactant gas. The results are shown in FIG. 3.

The conversion of butyric acid increased with temperature while the selectivity to propane remained very high. Minimal cracking products were observed at elevated temperatures (400° C.). The analysis of the condensed liquid from the separator indicated no other liquid phase products. Some deactivation was observed while the reaction temperature was maintained at 400° C. This is reflected in the lower conversion to propane upon cycling the temperature back down to 350° C.

Tests carried out using lower space velocities (WHSV=0.06-0.24 $h^{-1}$) with both unreduced and reduced Pd/C catalysts using He and 5% $H_2$/He as the carrier gas at 90 psig exhibited high selectivity for decarboxylation and dehydrogenation, with >95 vol. % of the $CO_2$-free gaseous products being propane and propylene. Other hydrocarbons observed in the gas product mixture were very small amounts of methane and ethane (i.e., products of subsequent carbon cracking reactions) and trace amounts of butane (<0.3 vol. %, product of hydrogenation of butyric acid). Upon comparing the amount of $CO_2$ to the $C_3$ hydrocarbons in the product gas stream, a molar ratio of 0.93 $CO_2$ to 1.0 (propane and propylene) was observed. Butyric acid was the only organic compound found in the liquid stream exiting the bottom of the condenser.

EXAMPLE 3

A Pt-based catalyst was prepared on multi-walled carbon nanotubes (MWNT) obtained from Cheap Tubes, Inc., (length: 10-30 μm long; 20-30 nm OD). A 1 wt % Pt/MWNT catalyst was prepared by incipient wetness impregnation as described in Example 1. Prior to impregnation, the MWNTs were treated in nitric acid at 120° C. for 4 hours in order to create acidic surface functionality. The catalyst was reduced under 99.99% hydrogen at 400° C. for 30 minutes using a ramp of 1° C. per minute. After reduction, the temperature was reduced to a reaction temperature of 327° C. The reaction was carried out at a space velocity of 9 $h^{-1}$. Some steady catalyst deactivation was observed as the butyric acid conversion decreased over the course of 48 hours. However, the selectivity to propane remained very high, at a minimum of ~92%.

EXAMPLE 4

A Pt-based catalyst, 1 wt % Pt/L-Zeolite, was prepared using the incipient wetness impregnation technique described in Example 1. The L-Zeolite support (pore volume~0.7 mL/g) was impregnated with $Pt(NH_3)_4(NO_3)_2$. The catalyst (0.2 g) was reduced at 300° C. (using a ramp of 2° C. per minute) under 99.99% $H_2$ gas for 30 minutes under atmospheric pressure. The reaction was conducted using the pretreatment gas as the carrier/reactant and the temperature was varied from 300° C. to 400° C. at a space velocity of 0.9 $h^{-1}$ (based on catalyst loading and acid flow). The highest butyric acid conversion of ~50% was observed at 400° C. The selectivity to propane was maintained at 97-100% throughout the reaction.

EXAMPLE 5

A 3 wt % $Au/Co_3O_4$ catalyst was prepared in house. The cobalt oxide powder was prepared in nanoparticle (4-5 nm size) form according to a surfactant-free preparation method described in *Nanotech*. 18 (2007) 435-602 and the gold was added by a urea-based deposition-precipitation technique aimed at dispersing the gold on the surface of the support, e.g. following the method described in J. Phys. Chem. B 106

(2002) 7634-7642. The catalyst was tested for the decarboxylation of a 30 wt % aqueous butyric acid feed. The catalyst was reduced at 250° C. (heating at 2° C. per minute) for 30 minutes under hydrogen gas. The reaction was carried out in the pretreatment gas (99.99% hydrogen) under atmospheric pressure. The temperature was varied from 250° C. to 400° C. The space velocity based on the butyric acid solution flow rate and the catalyst loading was 1.8 $h^{-1}$. The catalyst was active at higher temperatures, reaching a total conversion of 15% at 400° C., with the highest selectivity to propylene (~55%). Selectivity to other hydrocarbon gas products was observed, including propane (~20%), ethane (~4%), ethylene (~6%) and methane (~15%), indicating some degree of cracking.

The above examples demonstrate the suitability of several supported metal catalyst systems for the decarboxylation of aqueous solutions of short-chain carboxylic acids to produce gaseous hydrocarbon fuels. Depending on the choice of metal and its particle size and loading amount as well as the choice of the support, the decarboxylation can take place at mild conditions of pressure and temperature. In some cases, the carrier gas can be hydrogen-free. Examples of the carrier gas include but are not limited to an inert gas (He or nitrogen) and part of the $CO_2$.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of decarboxylating a $C_{2-6}$ carboxylic acid or a $C_{2-6}$ carboxylate, the method comprising:
    providing a solution containing a $C_{2-6}$ carboxylic acid or a $C_{2-6}$ carboxylate that is derived from biomass; and
    contacting the solution with a solid catalyst to form a $C_{1-5}$ hydrocarbon.

2. The method of claim 1, wherein the contacting step is performed at 200° C.-500° C. and at 1-30 atm.

3. The method of claim 1, wherein the contacting step is performed at 200-400° C. and at 1 atm.

4. The method of claim 2, wherein the solution is carried by a gas to effect contact with the solid catalyst.

5. The method of claim 4, wherein the gas is hydrogen, an inert gas, or a mixture thereof.

6. The method of claim 2, wherein the solid catalyst includes a metal and a substrate.

7. The method of claim 6, wherein the metal is Fe, Co, Ni, Mn, Ru, Rh, Pd, Re, Os, Ir, Pt, Sn, Cu, Ag, Au, or a combination thereof.

8. The method of claim 7, wherein the metal is Co, Cu, Pt, Pd, Sn, Re, Au, or a combination thereof.

9. The method of claim 8, wherein the metal is Au.

10. The method of claim 6, wherein the solution is carried by a gas to effect contact with the solid catalyst.

11. The method of claim 10, wherein the gas is hydrogen, an inert gas, or a mixture thereof.

12. The method of claim 6, wherein the substrate is a metal oxide, a metal sulfide, a metal nitride, a metal carbide, a zeolite, a molecular sieve, a perovskite, a clay, or a combination thereof.

13. The method of claim 12, wherein the metal is Fe, Co, Ni, Mn, Ru, Rh, Pd, Re, Os, Ir, Pt, Sn, Cu, Ag, Au, or a combination thereof.

14. The method of claim 6, wherein the substrate is a carbonaceous material.

15. The method of claim 14, wherein the metal is Fe, Co, Ni, Mn, Ru, Rh, Pd, Re, Os, Ir, Pt, Sn, Cu, Ag, Au, or a combination thereof.

16. The method of claim 14, wherein the carbonaceous material is activated carbon, carbon black, graphite, charcoal, carbon nanotubes, carbon fibers, or a combination thereof.

17. The method of claim 14, wherein the carbonaceous material includes carbon nanotubes.

18. The method of claim 17, wherein the metal is Fe, Co, Ni, Mn, Ru, Rh, Pd, Re, Os, Ir, Pt, Sn, Cu, Ag, Au, or a combination thereof.

19. The method of claim 1, wherein the biomass is a plant or a photosynthetic organism or a part thereof.

20. The method of claim 1, wherein the biomass is a carbohydrate.

21. The method of claim 19, wherein the solution is carried by a gas to effect contact with the solid catalyst and the contacting step is performed at 200° C.-500° C. and at 1-30 atm.

22. The method of claim 21, wherein the solid catalyst includes a metal selected from the group consisting of Fe, Co, Ni, Mn, Ru, Rh, Pd, Re, Os, Ir, Pt, Sn, Cu, Ag, and Au.

23. The method of claim 1, wherein the solution is an aqueous solution.

24. The method of claim 23, wherein the solution is carried by a gas to effect contact with the solid catalyst and the contacting step is performed at 200° C.-500° C. and at 1-30 atm.

25. The method of claim 24, wherein the solid catalyst includes a metal selected from the group consisting of Fe, Co, Ni, Mn, Ru, Rh, Pd, Re, Os, Ir, Pt, Sn, Cu, Ag, and Au.

* * * * *